United States Patent
Scaccabarozzi

(10) Patent No.: US 9,588,085 B2
(45) Date of Patent: Mar. 7, 2017

(54) DEVICE AND SYSTEM FOR ULTRASONIC INSPECTION

(71) Applicant: General Electric Company, Schenectady, NY (US)

(72) Inventor: Luca Scaccabarozzi, Cologne (DE)

(73) Assignee: General Electric Company, Schenectady, NY (US)

( * ) Notice: Subject to any disclaimer, the term of this patent is extended or adjusted under 35 U.S.C. 154(b) by 558 days.

(21) Appl. No.: 13/903,648

(22) Filed: May 28, 2013

(65) Prior Publication Data

US 2014/0352439 A1    Dec. 4, 2014

(51) Int. Cl.
G01N 29/04        (2006.01)
G01N 29/24        (2006.01)
G01N 29/28        (2006.01)

(52) U.S. Cl.
CPC ............ *G01N 29/04* (2013.01); *G01N 29/24* (2013.01); *G01N 29/28* (2013.01); *G01N 2291/106* (2013.01)

(58) Field of Classification Search
CPC .. G01N 29/28; G01N 29/24; G01N 2291/106; G01N 2291/2636; G01N 29/265
USPC ........ 73/623, 31.01, 622, 640; 376/249, 250
See application file for complete search history.

(56) References Cited

U.S. PATENT DOCUMENTS

| | | | |
|---|---|---|---|
| 4,218,923 A | | 8/1980 | Triplett et al. |
| 4,920,804 A | * | 5/1990 | Iwamoto ............... G01N 29/265 73/623 |
| 5,419,195 A | | 5/1995 | Quinn |
| 5,454,267 A | * | 10/1995 | Moreau ................ G01N 29/221 73/623 |
| 5,565,633 A | * | 10/1996 | Wernicke ............... G01N 27/82 324/220 |

(Continued)

FOREIGN PATENT DOCUMENTS

| DE | 19641888 A1 | 5/1998 |
|---|---|---|
| DE | 202004013045 U1 | 8/2004 |

(Continued)

OTHER PUBLICATIONS

Invitation to Pay Additional Fees issued in connection with corresponding PCT/US2014/038754 on Sep. 24, 2014.

*Primary Examiner* — Michael A Lyons
*Assistant Examiner* — Suman K Nath
(74) *Attorney, Agent, or Firm* — Barclay Damon, LLP

(57) ABSTRACT

This disclosure describes embodiments of a probe assembly and an inspection system for ultrasonic inspection. Designs for the probe assembly package components to fit into a bore of a hollow target. These designs may incorporate electronics to generate waves and to detect a wide selection of anomalies (e.g., transversal crack, longitudinal crack, and volumetric flaws) that can form in the hollow target. The probe assembly provides support structure to manipulate and operate these electronics in the bore. This support structure facilitates communication of signals, e.g., from transducer elements that operate as a phased array. The probe assembly also includes a fluid circulating system and coupling system that permits the probe device to detach and reattach to match the probe device (and other parts of the probe assembly) to the size of the bore. These systems allow for fluid and electrical signals to circulate through the probe assembly.

9 Claims, 11 Drawing Sheets

(56) References Cited

U.S. PATENT DOCUMENTS

| | | | |
|---|---|---|---|
| 6,442,997 B1 | 9/2002 | Megerle et al. | |
| 6,487,922 B1 * | 12/2002 | Bauer | G01N 29/225 |
| | | | 356/3.03 |
| 8,424,385 B2 * | 4/2013 | Park | F22B 37/005 |
| | | | 376/248 |
| 2005/0155410 A1 * | 7/2005 | Manoosingh | G01N 29/022 |
| | | | 73/31.01 |
| 2011/0125462 A1 | 5/2011 | Petrosky et al. | |
| 2011/0255373 A1 * | 10/2011 | Gueugnaut | G01N 29/225 |
| | | | 367/99 |

FOREIGN PATENT DOCUMENTS

| | | | | |
|---|---|---|---|---|
| GB | 2255825 A | * | 11/1992 | G01N 29/223 |
| WO | WO-2012167380 | | 12/2012 | |

* cited by examiner

DEVICE AND SYSTEM FOR ULTRASONIC INSPECTION

BACKGROUND OF THE INVENTION

The subject matter disclosed herein relates to ultrasonic inspection and, in certain embodiments, to a device and system for use to perform ultrasonic inspection.

Ultrasonic inspection employs a probe device to detect anomalies that are not readily apparent during visual inspection of a target. This probe device can incorporate one or more transducers that generate acoustic waves in response to stimuli, e.g., electrical waveform pulses. The stimuli energize the transducers, which in turn emit the acoustic waves in various form. Compression waves are useful to detect volumetric flaws, which are found inside of the material of the target. Shear waves can help identify cracks (e.g., transversal cracks) and notches (e.g., longitudinal notches) that develop on the outer surface of the target. The probe device often includes a piece of material, or "wedge," that covers the transducer elements. The wedge acts as a barrier to protect the transducers from damage and as a medium, which conducts the acoustic waves from the transducers to the surface of the target.

Inspection of pipes, tubes, axles, and other elongated targets introduce challenges that require robust probe devices and inspection systems. The probe devices may need to utilize arrangements of several transducers that generate acoustic waves of a specific form (e.g., compression, shear, etc.) to detect certain types of anomalies. Moreover, to perform an adequate and thorough inspection, the system needs to position the probe device in various locations along the length of the target. The system also needs to interrogate the circumferential structure at each location along the length of the target.

Unfortunately, space limitations in and around the target may constrain the size and/or scope of actuating mechanisms the system employs to move the probe device. These limitations may prevent use of elongated rods that can reach into the bore and/or central opening of the target to position the probe device. Dimensions of the bore may further restrict proper cabling and/or peripheral devices that are necessary to communicate signals and/or fluids with the probe device. These restrictions can prevent use of, for example, phased array ultrasonics, which deploy multiple transducers to generate and dynamically change the direction and focus of acoustic waves.

The discussion above is merely provided for general background information and is not intended to be used as an aid in determining the scope of the claimed subject matter.

BRIEF DESCRIPTION OF THE INVENTION

The disclosure below describe improvement in ultrasonic inspection and, in particular, probe assemblies and inspection systems for non-destructive testing of hollow target, e.g., axles, pipes, tubes, etc. Designs for the probe assemblies may incorporate electronics to generate waves and to detect a wide selection of anomalies (e.g., transversal crack, longitudinal crack, and volumetric flaws) that can form in the hollow target. The probe assemblies also provide support structure to manipulate and operate these electronics in the bore. This support structure facilitates communication of signals, e.g., from transducer elements that operate as a phased array. Examples of these signals define data that may indicate the presence of anomalies in the target.

This disclosure describes, in one embodiment, a device for ultrasonic inspection. The device comprises an elongated body having a first end, a second end, and a longitudinal axis extending therebetween. The device also has a probe element disposed proximate to the first end, the probe element comprising a first set of transducers. The device also has a probe control component coupled with the plurality of transducers, the probe control component has hardware to generate signals to selectively energize one or more of the plurality of transducers. The probe device further has a fluid circulating system extending from the first end to the second end of the elongated body, the fluid circulating system having a first port proximate to the probe element.

This disclosure also describes, in one embodiment, a probe for detecting an anomaly in a hollow target. The probe comprises a probe device having a first end and a second end, a probe element proximate to the first end, and a fluid circulating system with a first port proximate the first end and a second port proximate the second end. The probe also has a rotating component coupled with the second end of the probe device. The rotating component has a first part, a second part that rotates relative to the first part, and a coupling structure that couples the first part with the second part, the coupling structure configured to permit fluid and signal communication between the first part and the second part.

This disclosure further describes, in one embodiment, a system comprises a probe device comprising a plurality of transducer elements, a probe control component coupled with the plurality of transducer elements, and a fluid port proximate to the transducer elements. The system also has a tether component coupled with the probe device at a first end. The tether component comprises a first tether link and a second tether link that adjoin one another at a rotating joint. The system further has an actuator coupled with the tether component at a second end. The actuator comprises a spooling mechanism that houses the first tether link and the second tether link in a spooled configuration.

This brief description of the invention is intended only to provide a brief overview of the subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
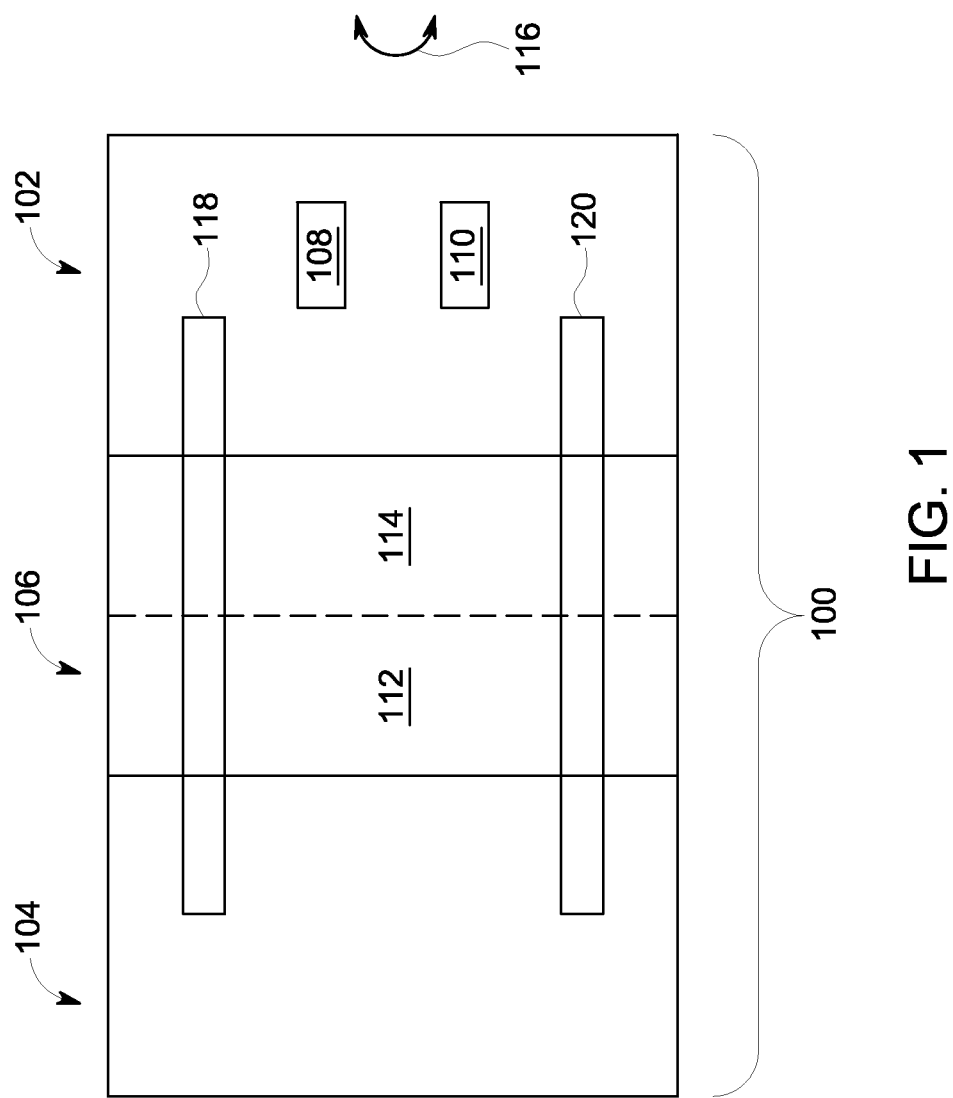
FIG. 1 depicts a schematic diagram of an exemplary embodiment of a probe assembly for non-destructive testing of a target.

FIG. 1 illustrates a schematic diagram of an exemplary embodiment of a probe assembly 100 that can generate ultrasonic signals for use in non-destructive inspection. The probe assembly 100 includes a probe component 102, an interface component 104, and a rotary component 106, which couples the probe device 102 to the interface component 104. The probe component 102 includes one or more probe elements (e.g., a first probe element 108) and a probe control component 110 that can exchange signals (e.g., electrical signals) with the first probe element 108. The rotary component 106 has a stationary part 112 and a rotating part 114. Examples of the parts 112, 114 can actively rotate the probe device 100, as generally indicated by the enumerated arrow 116. The probe assembly 100 also has one or more operating components (e.g., a fluid component 118 and a signal component 120). The operating components 118, 120 conduct inputs and outputs (e.g., fluids, electrical signals, etc.) between the probe device 100 and the interface component 104.

Designs for the probe component 102 package components to fit into a bore of a target, e.g., a pipe, tube, axle, etc. These designs incorporate electronics to generate waves and to detect a wide selection of anomalies (e.g., transversal crack, longitudinal crack, and volumetric flaws) that can form in the target. The probe assembly 100 provides support structure that permits the probe component 102 to operate in the bore. This support structure facilitates communication of signals, e.g., from the first probe element 108. Examples of these signals define data that may indicate the presence of anomalies in the target.

The probe elements (e.g., the first probe element 108) can comprise transducers of varying configurations. Exemplary construction of the first probe element 108 can include a pair of transducer arrays, each with a plurality of transducers. During operation, the transducers in each of the transducer arrays can generate and receive acoustic waves. In one embodiment, the transducers and/or transducer arrays operate as a phased array that are configured to dynamically change the direction and focus of acoustic waves. The phased array responds to signals to selectively energize one or more of the transducers in the transducer arrays. This operation is useful to identify particular types of anomalies, as contemplated herein.

Components of the probe assembly 100 facilitate communication of signals between the probe component 102 and the interface component 104. These components allow the probe device 102 to exchange signals with a peripheral device, e.g., a controller and/or system-level device. Examples of the peripheral devices can process the signals to generate a visual representation of the anomaly on a display. Construction of the probe assembly 100 can also facilitate movement (e.g., rotation) of the probe component 102. This feature permits the probe component 102 to rotate relative to the target, which is useful to aim and/or position the transducers in position to interrogate different angular portions of the target. In one embodiment, the construction utilizes various mechanical and electro-mechanical devices to couple the stationary part 112 and the rotating part 114 of the rotating component 106. These types of devices can maintain conduction of signals and fluids between the probe component 102 and the interface component 104 during rotation of the rotating part 114 relative to the stationary part 112.

Figure 2:
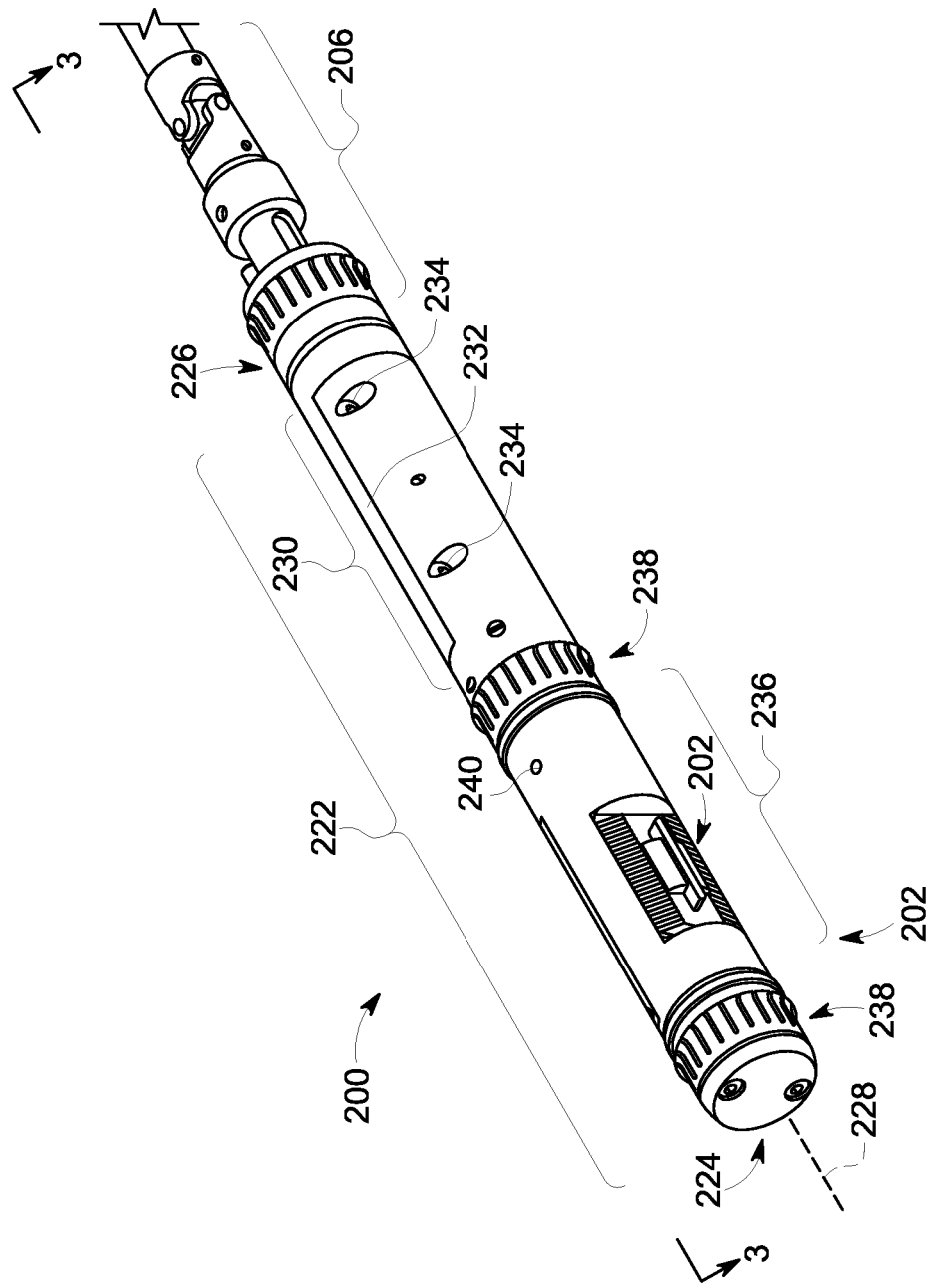
FIG. 2 depicts a perspective view of an exemplary embodiment of a probe assembly with a probe device that is useful to inspect small diameter hollow targets.

FIG. 2 depicts a perspective view of an exemplary embodiment of a probe assembly 200, which is shown in partial constructed form for purposes of example only. In one example of FIG. 2, the probe component 202 has an elongated body 222 with a first end 224, a second end 226, and a longitudinal axis 228 that extends therebetween. The second end 226 of the elongated body 222 includes an interface area 230 with a recess 232, or similar feature, to receive a portion of the rotary component 206. In one example, the probe assembly 200 can utilize one or more fasteners 234 to secure this portion of the rotating component 206 at the interface area 230. At the first end 224, the elongated body 222 forms an inspection area 236 that is bound by a pair of boundary elements 238 spaced longitudinally apart from one another along the axis 228. The inspection area 236 includes one or more rearward fluid ports 240 that open onto the surface of the elongated body 222.

Figure 3:
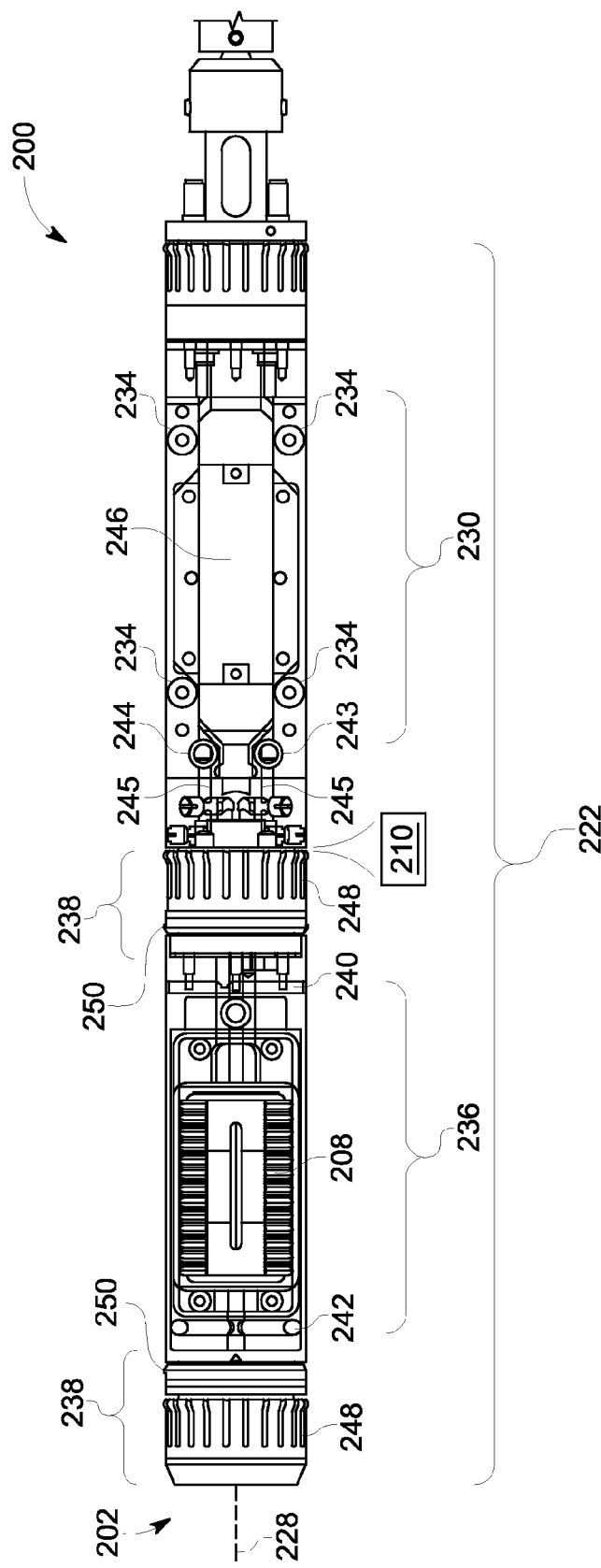
FIG. 3 depicts a side, elevation, cross-section view of the probe assembly of FIG. 2.

The diagram of FIG. 3 illustrates a side, partial cross-section view of the probe assembly 200 taken at line 3-3 of FIG. 2. The probe component 202 has a fluid circulating system that includes the rearward fluid ports 240 and one or more forward fluid ports 242 disposed in the inspection area 236. At the interface area 230, the probe component 202 can include one or more fluid connectors (e.g., a first fluid connector 243 and a second fluid connector 244) that couple with, respective, the rearward fluid ports 240 and the forward fluid ports 242. In one example, the probe device 202 incorporates one or more fluid carrying elements 245 that allow fluid to flow between the ports 240, 242 and the ports 243, 244. The interface area 230 can also have one or more connector elements (e.g., connector element 246) that couples with the probe control component 210. At the inspection area 236, the boundary elements 238 can include a first annular sleeve 248 and a second annular sleeve 250. In one embodiment, the first annular sleeve 248 comprises brass, although other materials (e.g., plastic, rubber, and/or other pliable material) in a form to circumscribe at least part of the elongated body 222. This material contacts an inner surface of the target to center the probe device 200 in the target. Examples of the second annular sleeve 250 can comprise a rubber ring (e.g., an o-ring) that can rotate independent of the elongated body 222. Additional details for the construction of the annular sleeves 248, 250 are found in FIG. 10, discussed further below.

Configurations of the elongated body 222 and the second annular sleeve 250 form a circumferential cavity and/or reservoir in the inspection area 236. The fluid circulating system circulates fluid (e.g., oil) into and out of this circumferential cavity. The rubber rings (e.g., second annular sleeve 250) contain the fluid in the circumferential cavity. This fluid acts as a medium favorable for conducting and/or coupling acoustic waves from the probe component 202 to the target. Examples of the fluid carrying elements 245 include tubing and/or hoses, although this disclosure contemplates other constructions that incorporate features (e.g., holes, bores, etc.) in the material structure of the elongated body 222. Collectively, the fluid carrying elements 245 can form a network to allow fluid to flow, e.g., between the ports 240, 242 and the ports 243, 244.

During operation, the fluid disperses into the inspection area 236 forming a thin layer between a surface of the target and the outer surface of probe device 200, e.g., a surface of the elongated body 222 and/or the probe element 208 in the inspection area 236. The first annular sleeve 248 and the second annular sleeve 250 can contact and/or engage with the surface of the target. Examples of the second annular sleeve 250 can comprise a ring and/or gasket (made of materials compatible with the fluid) that engage the surface of the target to prevent fluid from migrating out of the reservoir and along the outer edges of the elongated body. The second annular sleeve 250 can couple with one or more bearings (not shown) to permit the elongated body 222 to rotate relative to the second annular sleeve 250, thereby maintaining an appropriate seal as the probe assembly 200 operates to change direction of the probe component 202 during an inspection of the target.

In one embodiment, the elongated body 222 may house the probe control component 210 to incorporate many of the functions into the probe component 202 that are necessary to operate transducers, e.g., as a phased array. This disclosure contemplates other positions for the probe control component, e.g., in the rotary component 306. Examples of the probe control component 210 include circuitry and similar electronics and hardware, including discrete devices (e.g., transistors, resistors, etc.), processors (e.g., ASIC), and memory (e.g., RAM, ROM, etc.). This circuitry can embed and execute certain executable instructions (e.g., software, firmware, etc.) to generate signals that correspond to transmit and receive functions of phased array devices. The hardware and instructions of the probe control component 210 reduces the number of cables and other devices that are necessary to operate the probe elements to perform an inspection.

Figure 4:
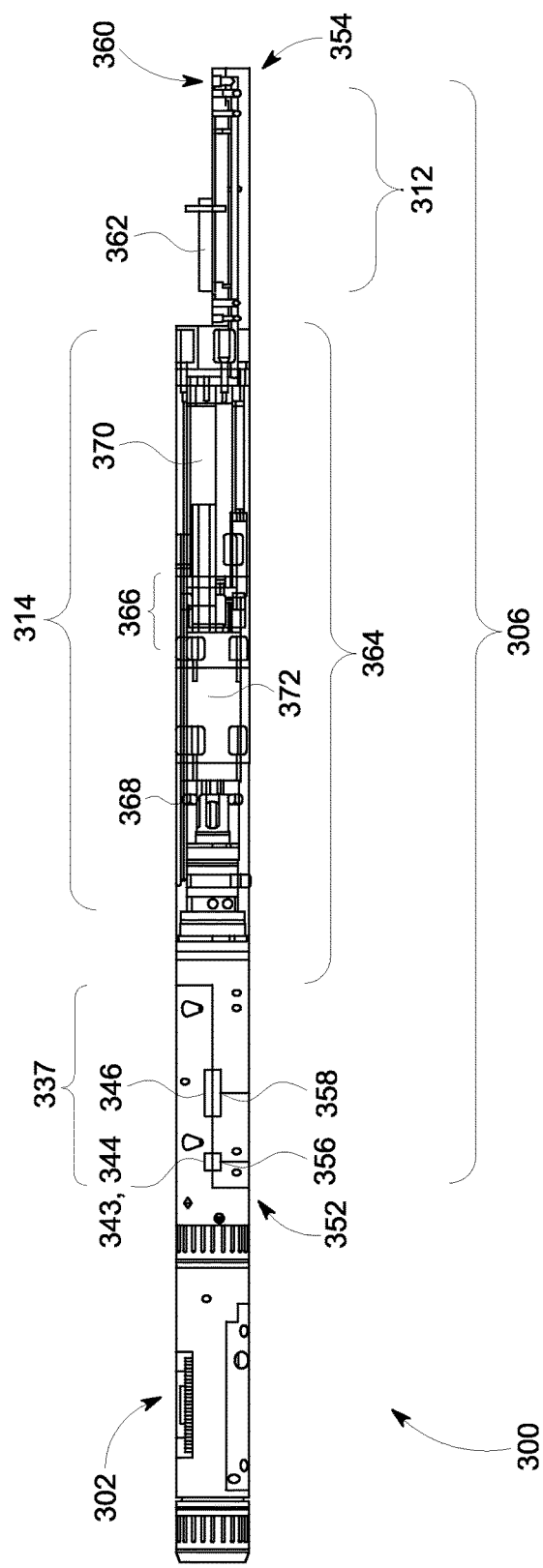
FIG. 4 depicts a side, elevation, cross-section view of an exemplary embodiment of a probe assembly with a rotary component for use to engage and rotate a probe component.

FIG. 4 illustrates a side, partial perspective view of an exemplary embodiment of a probe assembly 300 to illustrate one construction for the rotary component 306. In one embodiment, the rotary component 306 has a pair of receiving areas (e.g., a first receiving area 352 and a second receiving area 354) disposed on opposite ends of the structure. In the first receiving area 352, the rotary component 306 includes one or more forward interface ports 356 and one or more forward interface connector elements 358. The second receiving area 354 includes one or more rearward interface ports 360 and one or more rearward interface connector elements 362. In one embodiment, the interface ports 356, 360 have different oil interfaces to allow for fluid flow in different direction, e.g., from the first receiving area 352 to the second receiving area 354 and from the second receiving area 354 to the first receiving area 352. One example of the flow pattern is shown in the schematic diagram of FIG. 11.

As also shown in FIG. 4, the rotary component 306 includes a coupling structure 364 that secures the stationary part 312 and the rotating part 314 together. The coupling structure 364 includes a rotary joint 366, one or more bearing components 368, and a drive system with a motor 370. The drive system can also include one or more gear elements, separate from and/or incorporated with the motor 370. Examples of the gear elements transfer rotary motion of the motor 370 to rotate the rotating part 314. The coupling structure 364 can also include a slip ring 372, or like rotary electrical joint, that conducts signals, e.g., between the forward interface connector element 358 and the rearward interface connector element 362. Designs for the slip ring 372 can vary according to the number of channels (e.g., the number of transducer elements of the probe device 202) and/or according to the required wires for the remote electronic device (e.g., probe control component 210). In one example, the joint 366 can incorporate one or more parts (e.g., a shaft) of the slip ring 372.

In one implementation, the interface area 337 of the probe component 302 engages the first receiving area 352 of the rotary component 306. This engagement can permit fluid and signal communication, e.g., via coupling of the ports 342 with the ports 356 and coupling of the connector element 346 with the connector element 358. The probe assembly 300 may utilize one or more fasteners (e.g., screws, bolts, etc.) and/or integrated mechanism that secure the probe component 302 in position on the rotary component 306.

The coupling structure 364 utilizes components and structure to allow movement of the rotary part 314 relative to the stationary part 312. Examples of this structure can rotate the rotary part 314, while maintaining fluid and signal connection to allow the probe component 302 to operate as necessary to perform inspection of the target. The arrangement of the rotary joint 366 may include components that mate, secure, and/or couple together to allow fluid and signals to pass, e.g., between the first receiving area 352 and the second receiving areas 354. Moreover, the rotary joint 366 may include a sensor element that provides a reference "null" position for rotation. Examples of the sensor element can be integrated or separate from the slip ring 372.

Figure 5:
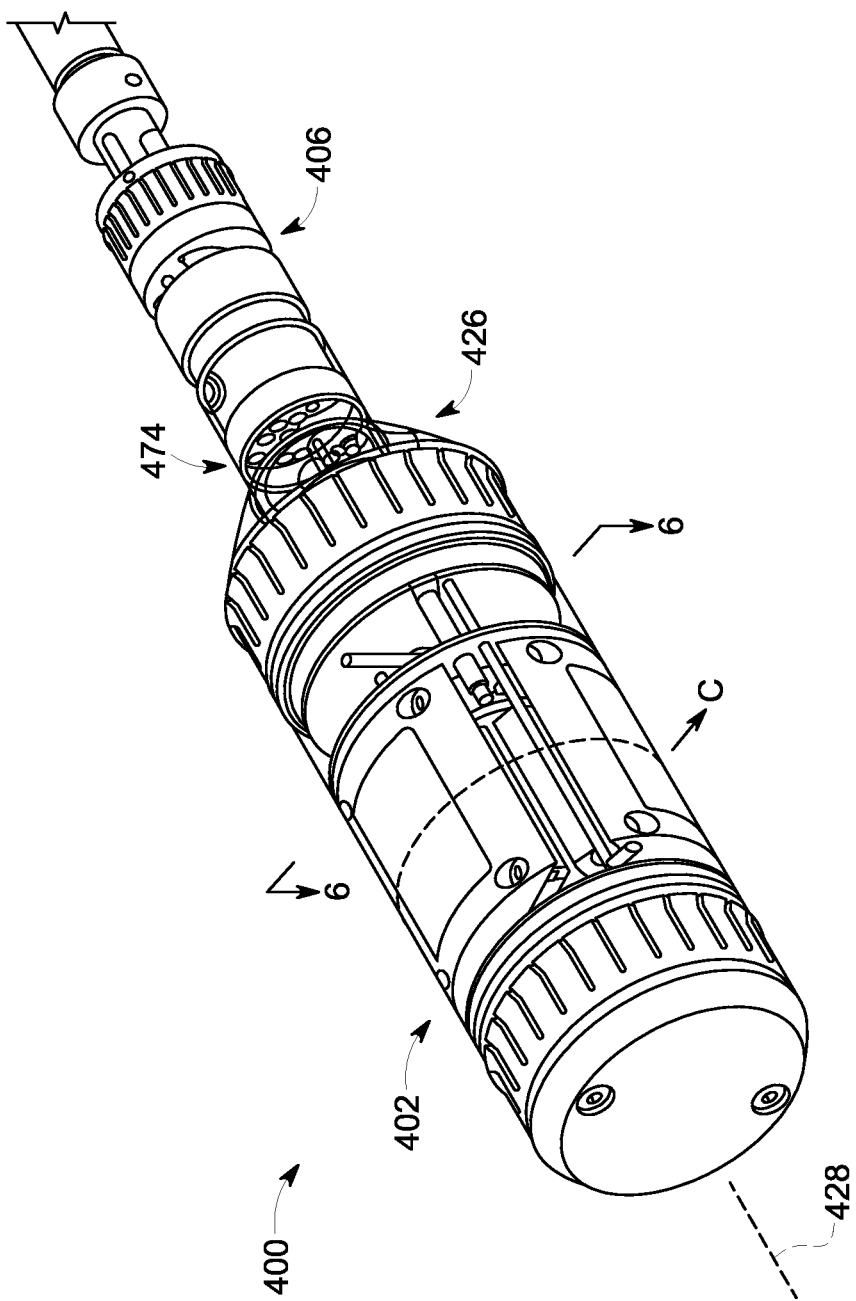
FIG. 5 depicts a perspective view of an exemplary embodiment of a probe assembly that is useful to inspect large diameter hollow targets.
Figure 6:
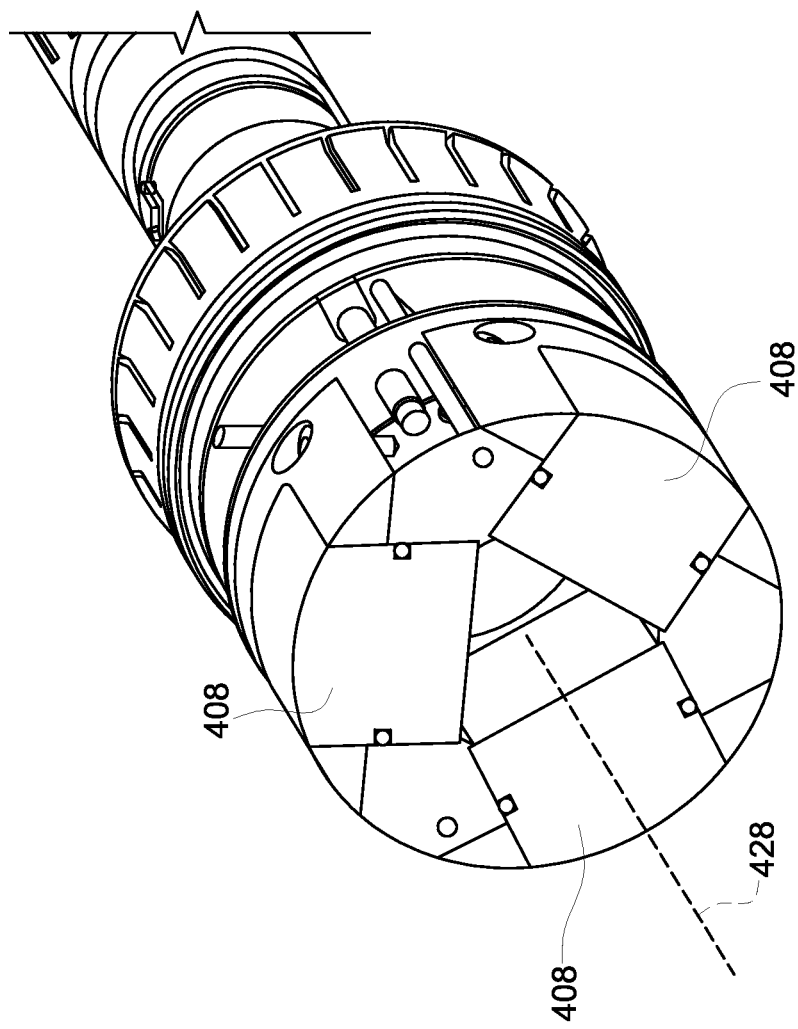
FIG. 6 depicts a front, cross-section view of the probe assembly of FIG. 5 to illustrate one configuration for probe elements in a probe component.

FIGS. 5 and 6 depict a perspective view of an exemplary embodiment of a probe assembly 400. In this embodiment, the probe component 402 is useful to perform inspection of targets with bore diameters from about 65 mm or greater. At the second end 426, the probe assembly 400 incorporates a plug-type interface 474 to couple the probe component 402 to the rotary component 406. Examples of plug-type interface 474 can utilize corresponding mating pins and sockets that can conduct signals and fluids, e.g., between the probe component 402 and the rotary component 406. As best shown in FIG. 6, which is a cross-section of the probe assembly 400 taken at line 6-6 of FIG. 5, the probe component 402 includes a plurality of probe elements 408 disposed circumferentially about the longitudinal axis 428.

Figure 7:
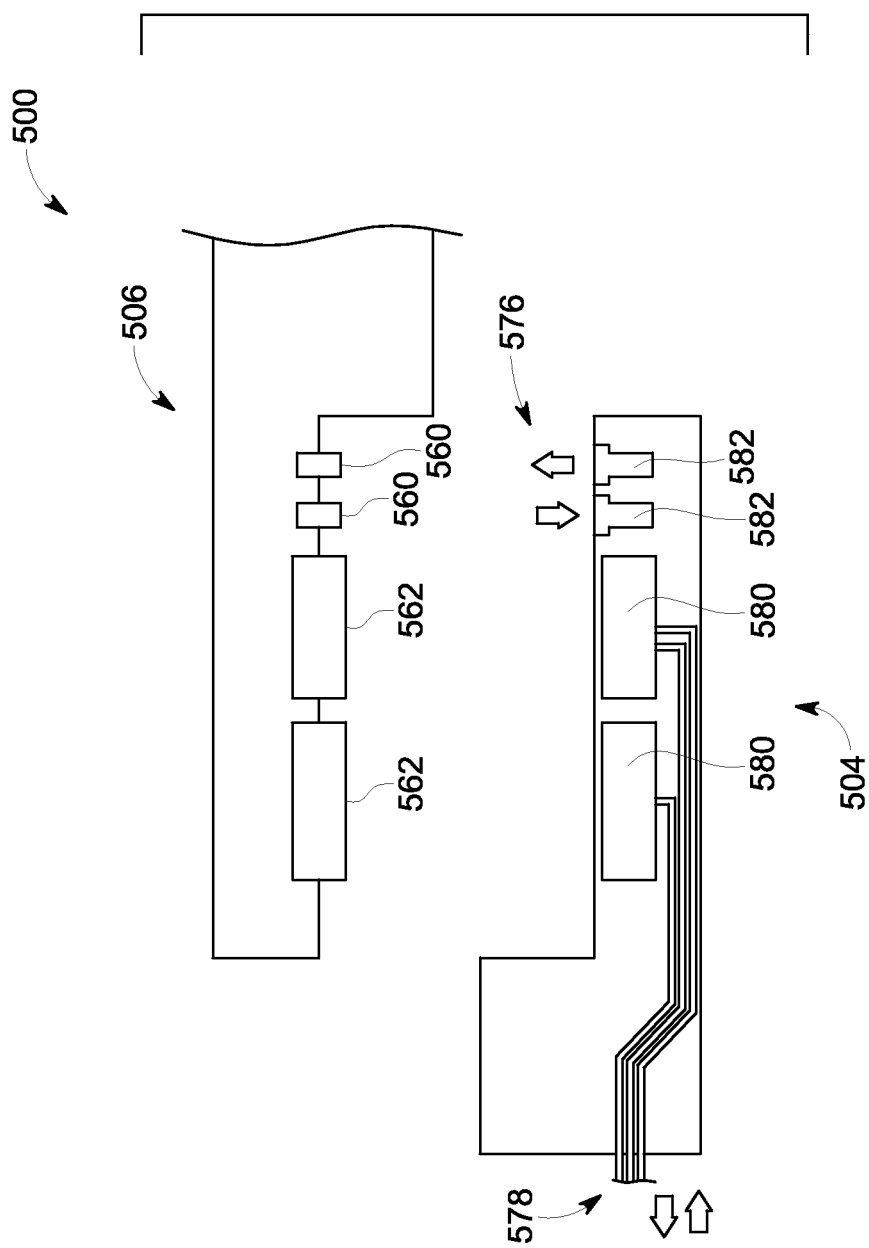
FIG. 7 depicts a side, elevation, cross-section view of an exemplary embodiment of a probe assembly with an interface component that can couple a probe component with an inspection system.

FIG. 7 depicts a side, cross-section view of an exemplary embodiment of a probe assembly 500 in a partial, exploded view to focus the discussion on the interface component 504. In one embodiment, the interface component 504 has a connecting area 576 and an input/output area 578. The connecting area 576 includes one or more connectors 580 and one or more fluid ports 582. In one implementation, the connecting area 576 couples with the second receiving area 554 on the rotary component 506. This configuration makes the necessary connections (e.g., the ports 582 connect with the ports 560 and the connectors 580 connect with the connectors 562) to allow fluid and signal communication between the interface component 504 and the rotary component 506. As set forth more below, the input/output area 578 can couple with one or more components of an inspection system. This connection allows the inspection system to communication with the probe components (e.g., probe components 102, 202, 302, 402) to perform inspection of the target.

Figure 8:
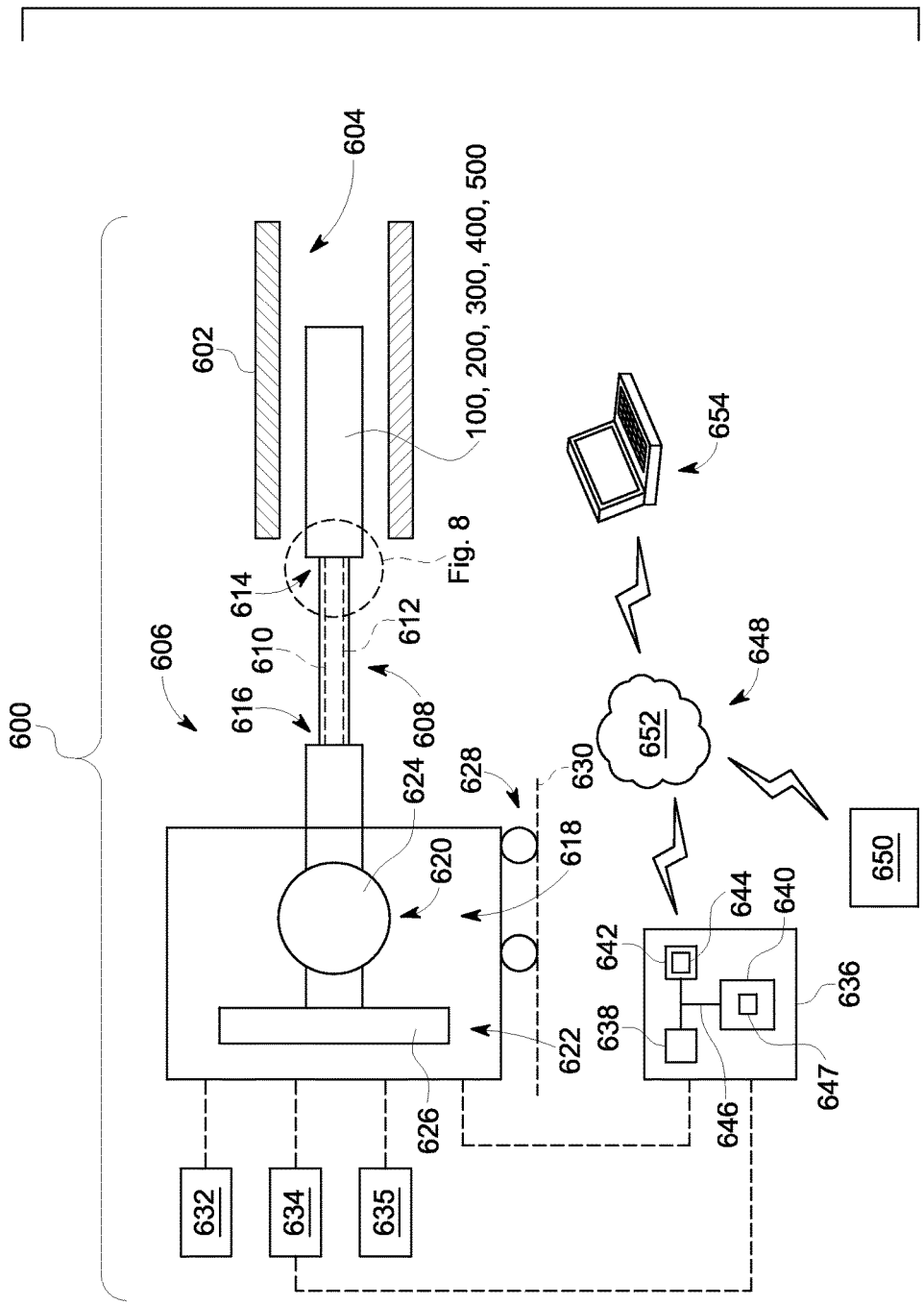
FIG. 8 depicts a schematic diagram of an inspection system for non-destructive testing.

The schematic diagram of FIG. 8 illustrates a side view of an inspection system 600 that can utilize a probe assembly (e.g., probe device 100, 200, 300, 400, 500) to inspect a target 602. Examples of the target 602 include hollow targets (e.g., pipes, tubes, axles, etc.) with an inner bore 604 that receives the probe assembly. The inspection system 600 includes a translating mechanism 606 with a tether component 608 that houses one or more coupling elements (e.g., a first coupling element 610 and a second coupling element 612). The tether component 608 couples at a first end 614 with the probe device, e.g., via an interface component (e.g., interface component 104, 504), and at a second end 616 to an actuating device 618.

Examples of the actuating device 618 can extend and retract the tether component 608 to translate the probe device from a first position proximate an opening to the inner bore 604 (as shown in FIG. 8) to a second position spaced apart from the bore and further interior of the bore 604. The actuating device 618 can include one or more actuators (e.g., a first actuator 620 and a second actuator 622) that facilitate movement of the probe device. The first actuator 620 can incorporate a spooling mechanism 624 that can store a portion of the tether component 608, e.g., when the probe device is in the first position. Examples of the second actuator 622 may include a linear actuator 626 that can change the elevation of the spooling mechanism 624 to present the probe device in appropriate position to enter the inner bore 604. In one embodiment, the translating mechanism 606 may further include one or more rolling elements 628 that afford the translating mechanism 606 with low friction contact with a surface 630 (e.g., a floor). This feature facilitates movement of the translating mechanism 606 to different locations, e.g., within a manufacturing and/or industrial setting.

As also shown in FIG. 8, the inspection system 600 can include one or more peripheral components (e.g., a fluid supply 632, a power supply 634, an actuator control 635, and a controller 636). The actuator control 635 can have an interface with control devices (e.g., buttons, switches, a joystick) to allow an end user to interface with the inspection system 600. These control devices can causes and/or direct movement of the probe assembly, flow of fluids, emergency shutoff, and similar functions. In one embodiment, the controller 636 has a processor 638, control circuitry 640, and memory 642, which can store one or more executable instructions 644, e.g., in the form of software and firmware that are configured to be executed by a processor (e.g., the processor 638). The controller 636 can also includes busses 646 to couple components (e.g., processor 638, control circuitry 640, and memory 642) of the controller 636 together. The busses 646 permit the exchange of signals, data, and information from one component of the controller 636 to another. The control circuitry 640 can include remote ultrasonic electronics 647 that can process signals from the probe assembly.

Examples of the controller can communicate with a network system 648 with one or more external servers (e.g., external server 650) and a network 652 that connects the controller 636 to the external server 650. This disclosure also contemplates configurations in which one or more programs and/or executable instructions (e.g., executable instructions 644) are found on the external server 650. The controller 636 can access these remotely stored items to perform one or more functions disclosed herein. In one embodiment, a computing device 654 may communicate with one or more of the controller 636 and the network 652, e.g., to interface and/or interact with the probe device and/or components of the inspection system 600, as desired.

Figure 9:
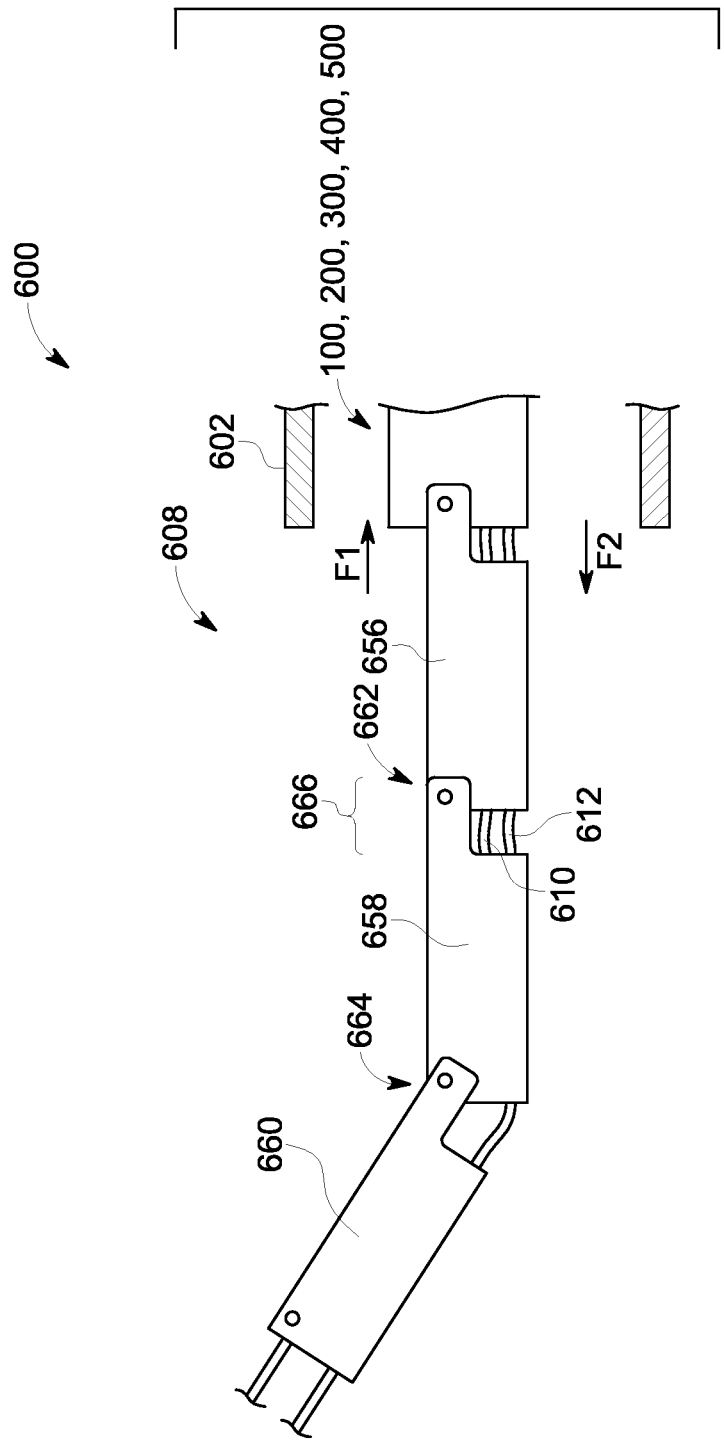
FIG. 9 depicts a side, elevation view of an exemplary tether component for use in the inspection system of FIG. 8 to move a probe assembly, e.g., probe assemblies of FIGS. 1, 2, 3, 4, 5, 6, and 7.

FIG. 9 illustrates a detail view of the inspection system 600 to illustrate one construction for the tether component 608. In FIG. 9, the tether component 608 includes a plurality of tether links (e.g., a first tether link 656, a second tether link 658, and a third tether link 660). The tether links 656, 658, 660 can have an adjoining end 662 and a receiving end 664. In one example, the adjoining end 662 forms a clevis 666, which fits around the receiving end 664 of the adjacent tether link 656, 658, 660. The tether links 656, 658, 660 are joined to form at least one degree of freedom to rotate relative to one another.

During operation, one or more actuators (e.g., spooling mechanism 624) applies force to the tether component 608. This force can push and pull on the tether component 608. Under the pushing force, the tether links 656, 658, 660 engage one another to form an elongated chain of sufficient stiffness to generate a pushing force (F1) against the probe device. This feature allows the inspection system 600 (FIG. 7) to change the position of the probe device, e.g., relative to the target 602. On the other hand, the pulling force will pull the tether links 656, 658, 660 into the spooling mechanism 624 (FIG. 7). The hinged joints that couple adjacent tether links 656, 658, 660 together allow the tether component 608 to collapse and, in one example, effectively wind into a collapsed configuration. This construction reduces the size of the tether component 608 that is necessary to reach the outer ends of the target 602 with the probe device. Examples of the tether links 656, 658, 660 can have a hollow and/or semi-hollow construction that allows the coupling elements 610, 612 to pass through the tether component 608 to couple with corresponding features on the input/output area (e.g., input/output area 578 of FIG. 7) on the interface component (e.g., interface component 504 of FIG. 7).

Figure 10:
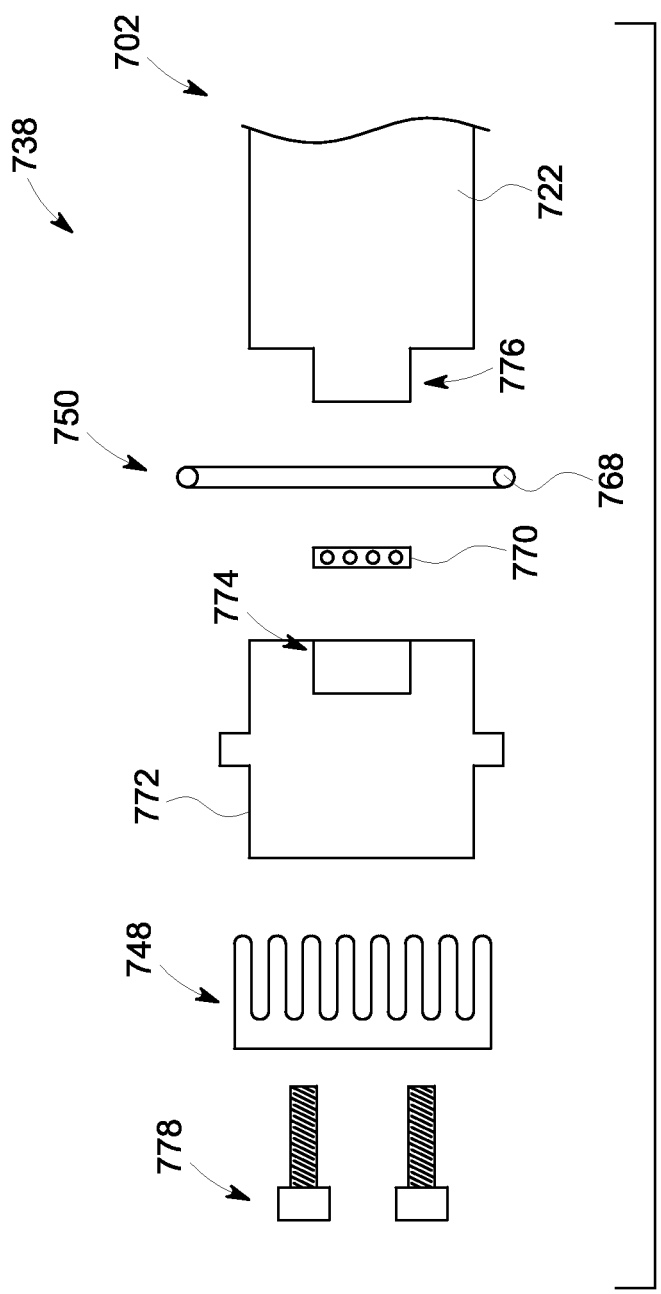
FIG. 10 illustrates a schematic diagram of a side, elevation view an exemplary boundary element for use in a probe assembly.

FIG. 10 depicts a schematic diagram of a side, elevation view of an exemplary boundary element 738. In one example, the boundary element 738 includes the first sleeve element 748 and the second sleeve element 750 in the form of a rubber o-ring 768. The boundary element 738 also includes a bearing 770 and a bushing 772 with an opening 774 to receive the bearing 770 therein. The bearing 770 can interface with a boss element 776, which can be found on the elongated body 722 of the probe device 702, as disclosed and contemplated herein. One or more fasteners 778 can couple the first sleeve element 702 with the bushing 772.

Figure 11:
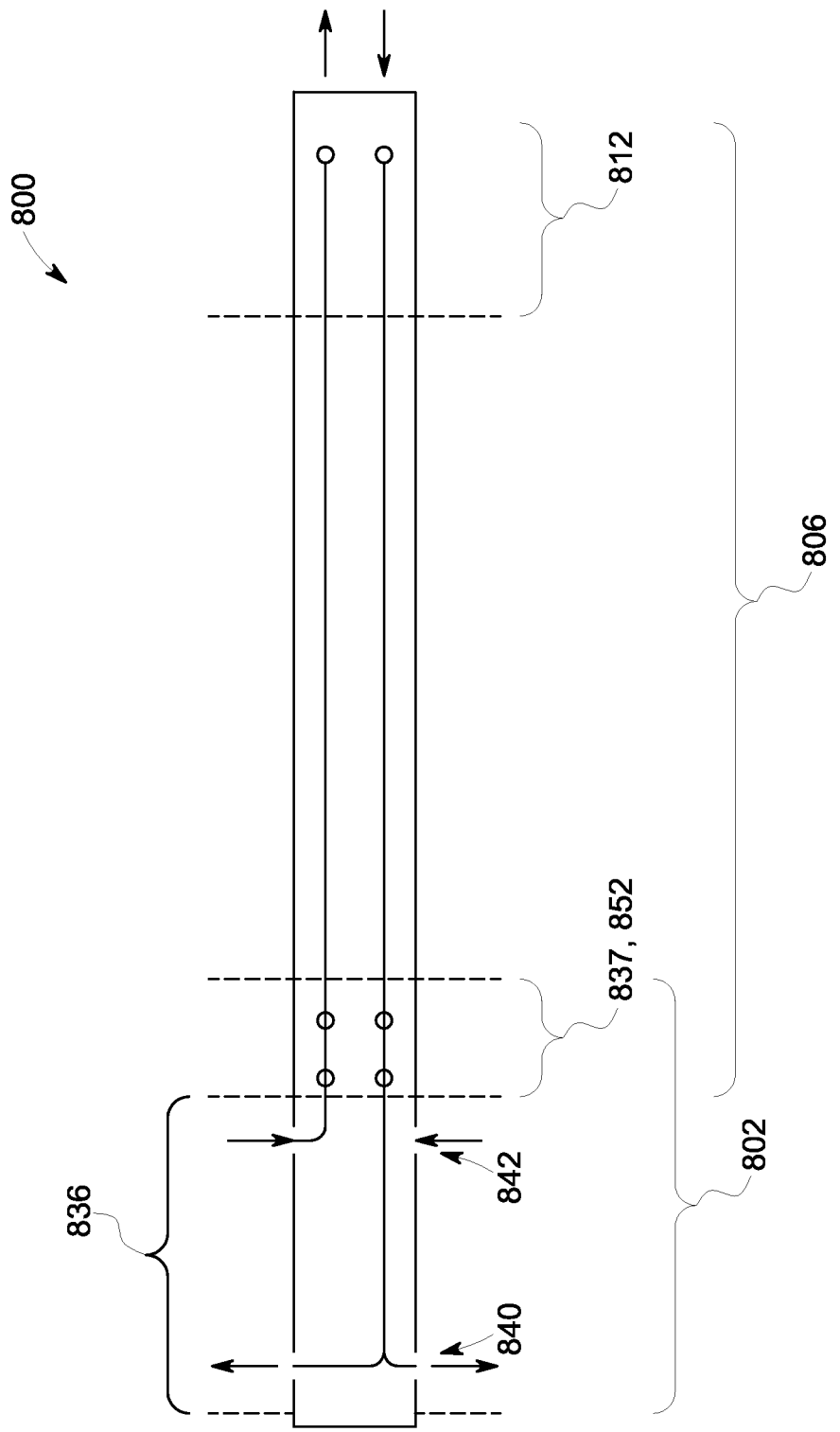
FIG. 11 illustrates a plan view of an exemplary embodiment of a probe assembly to illustrate an exemplary flow pattern for fluid through the probe assembly.

The schematic diagram of FIG. 11 illustrates a plan view of an exemplary embodiment of a probe assembly 800 to illustrate an exemplary flow pattern for fluid (e.g., oil) through the structure. As shown in FIG. 11, fluid can enter the probe assembly 800 at the stationary part 812 of the rotary component 806. The fluid can travel through the structure of the rotary component 806 to the interface area 837, 852 where the rotary component 806 couples with the probe component 802. The fluid continues through the probe component 802, where it ejects out of a first set of ports (e.g., forward ports 840) into the inspection area 836. In one embodiment, vacuum pressure can be used to draw the fluid into a second set of ports (e.g., rearward ports 842) to travel back, through the interface area 837, 852 and out of the stationary part 812. This fluid circulating system forms the thin oil layer (or film) in the inspection area 836. Examples of this layer are useful for conducting acoustic signals between the probe device 802 and the target.

As used herein, an element or function recited in the singular and proceeded with the word "a" or "an" should be understood as not excluding plural said elements or functions, unless such exclusion is explicitly recited. Furthermore, references to "one embodiment" of the claimed invention should not be interpreted as excluding the existence of additional embodiments that also incorporate the recited features.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A device for ultrasonic inspection, said device comprising:
   a body having a first end, a second end, and a longitudinal axis extending therebetween;
   a probe element disposed proximate to the first end of the body, the probe element comprising a first set of transducers;
   a probe control component coupled with the first set of transducers, the probe control component having hardware to generate signals to selectively energize one or more of the first set of transducers;
   a connector disposed proximate to the second end of the body, the connector coupled with the probe control component, wherein the connector is configured to exchange an electrical signal between the probe element and the probe control component;
   a rotary component coupling the first end of the device with the second end of the device, the rotary component comprising:
      a stationary part, the stationary part being disposed adjacent to the second end of the device;
      a rotating part that rotates relative to the stationary part, the rotating part being disposed adjacent to the first end of the device; and
      a coupling structure that rotatably couples the stationary part with the rotating part, the coupling structure configured to permit fluid and signal communication between the stationary part and the rotating part; and
   a fluid circulating system extending from the first end to the second end of the body, the fluid circulating system having a first port proximate to the probe element, wherein the fluid circulating system is configured to circulate fluid from the stationary part through the rotary component to the probe element notwithstanding relative rotation of the stationary part and the rotating part of the rotary component.

2. The probe of claim 1, further comprising a second port proximate to the connector.

3. The probe device of claim 2, wherein the body has a recess with a surface that receives the second.

4. The probe device of claim 1, further comprising boundary elements disposed circumferentially about the longitudinal axis and disposed longitudinally on either side of the probe element, wherein the boundary elements extend radially away from an outer surface of the body.

5. The probe device of claim 4, wherein the boundary elements form an inspection area between the boundary elements, and wherein the first port has an open end that is in fluid communication with the inspection area.

6. The probe device of claim 1, wherein the body has a cylindrical shape.

7. The probe device of claim 1, wherein the probe element comprises a first probe element incorporating the first set of transducers and a second probe element comprising a second set of transducers that is different from the first set of transducers.

8. The probe device of claim 7, wherein the probe control component couples with the first probe element and the second probe element, and wherein the probe control component comprises one or more executable instructions for operating one of the first set of transducers and the second set of transducers as a phased array.

9. The probe device of claim 8, wherein the executable instructions include executable instructions for operating the first set of transducers and the second set of transducers as the phased array.

* * * * *